US009809886B2

(12) United States Patent
Clark et al.

(10) Patent No.: US 9,809,886 B2
(45) Date of Patent: Nov. 7, 2017

(54) METHOD OF MACHINING A GAS TURBINE ENGINE COMPONENT

(71) Applicant: ROLLS-ROYCE PLC, London (GB)

(72) Inventors: Daniel Clark, Derby (GB); Andrew Robert Walpole, Derby (GB)

(73) Assignee: ROLLS-ROYCE plc, London (GB)

( * ) Notice: Subject to any disclaimer, the term of this patent is extended or adjusted under 35 U.S.C. 154(b) by 162 days.

(21) Appl. No.: 14/843,304

(22) Filed: Sep. 2, 2015

(65) Prior Publication Data

US 2016/0083852 A1    Mar. 24, 2016

(30) Foreign Application Priority Data

Sep. 18, 2014 (GB) .................................. 1416483.4

(51) Int. Cl.
| | |
|---|---|
| C23F 1/00 | (2006.01) |
| C23F 1/12 | (2006.01) |
| F01D 5/28 | (2006.01) |
| F01D 9/02 | (2006.01) |
| F23R 3/00 | (2006.01) |
| F01D 5/00 | (2006.01) |
| F01D 5/18 | (2006.01) |
| G01N 21/956 | (2006.01) |

(52) U.S. Cl.
CPC ............... *C23F 1/00* (2013.01); *C23F 1/12* (2013.01); *F01D 5/28* (2013.01); *F01D 9/02* (2013.01); *F23R 3/002* (2013.01); *B23P 2700/06* (2013.01); *F01D 5/005* (2013.01); *F01D 5/186* (2013.01); *F05D 2230/10* (2013.01); *G01N 21/95692* (2013.01)

(58) Field of Classification Search
CPC ...... C23F 1/00; C23F 1/12; F01D 5/28; F01D 9/02; F23R 3/002
See application file for complete search history.

(56) References Cited

U.S. PATENT DOCUMENTS

| | | | | |
|---|---|---|---|---|
| 6,156,666 A | * | 12/2000 | Tokushima | ............... C23F 4/00 257/E21.311 |
| 6,315,819 B1 | | 11/2001 | Tokushima | |
| 7,229,563 B2 | * | 6/2007 | Chen ......................... | C23F 4/00 216/13 |

(Continued)

FOREIGN PATENT DOCUMENTS

| | | |
|---|---|---|
| EP | 0943916 A2 | 9/1999 |
| EP | 1221604 A2 | 7/2002 |
| EP | 2 253 744 A2 | 11/2010 |

(Continued)

OTHER PUBLICATIONS

Jan. 20, 2016 Search Report issued in European Patent Application No. 15183495.

(Continued)

*Primary Examiner* — Duy Deo
(74) *Attorney, Agent, or Firm* — Oliff PLC

(57) ABSTRACT

A method of machining a nickel containing alloy gas turbine engine component (34) comprises applying a material removal gas comprising gaseous carbon monoxide at a nickel carbonyl gas forming temperature such as 50 to 60° C. to a surface of the component to form a nickel carbonyl gas, and thereby remove a surface layer from at least part of the component.

11 Claims, 2 Drawing Sheets

(56) References Cited

U.S. PATENT DOCUMENTS 7,955,515 B2 * 6/2011 Raghuram ........ H01L 21/31122
216/67

FOREIGN PATENT DOCUMENTS

| GB | 2473099 A | 3/2011 |
|---|---|---|
| GB | 2487930 A | 8/2012 |
| WO | 2007/008901 A2 | 1/2007 |

OTHER PUBLICATIONS

Mar. 18, 2015 Search Report issued in GB Patent Application No. 1416483.4.

* cited by examiner

METHOD OF MACHINING A GAS TURBINE ENGINE COMPONENT

FIELD OF THE INVENTION

The present invention relates to a method of machining a component of a gas turbine engine. In particular, though not exclusively, the method relates to testing of cooling holes in a turbine blade of a gas turbine engine, and adjusting the dimensions of said cooling holes in accordance with the test.

BACKGROUND TO THE INVENTION

FIG. 1 shows a gas turbine engine 10. The engine 10 comprises an air intake 12 and a propulsive fan 14 that generates two airflows A and B. The gas turbine engine 10 comprises, in axial flow A, an intermediate pressure compressor 16, a high pressure compressor 18, a combustor 20, a high pressure turbine 22, an intermediate pressure turbine 24, a low pressure turbine 26 and an exhaust nozzle 28. A nacelle 30 surrounds the gas turbine engine 10 and defines, in axial flow B, a bypass duct 32.

Some of the components of the gas turbine engine may comprise nickel alloys, such as nickel super-alloys. One example nickel alloy component comprises a turbine blade 34 shown in FIG. 2. The blade 34 forms part of the high pressure turbine 22 and comprises a suction side 36 and a pressure side 38, as well as leading and trailing edges 40, 42, a root 44 at a radially inner end, and a tip 46 at a radially outer end.

The turbine blade 34 includes a plurality of cooling holes 48 leading from an internal passage 50, which extends from the root 44 to the tip 46. The holes 48 provide cooling air provided from one of the compressors 16, 18 to prevent softening of the metal in use, since gases flowing over the turbine blades 34 are generally at a very high temperature.

The positioning and size of the cooling holes 48 must be selected to ensure that no part of the blade 34 is subject to excessively high temperatures during use, while minimising use of cooling air, since the cooling air bled from the compressors 16, 18 is essentially lost to the thermodynamic cycle of the engine 10. Essentially therefore, excessive use of cooling air leads to increased specific fuel consumption. During the design stage of a new blade 34, it is therefore generally necessary to test a blade 34 to determine the amount of cooling provided by the cooling holes 48 during different conditions.

In one known testing method, steam is forced through the passage 50 to emerge from the cooling holes 48, and the flow through the holes 48 is measured. The holes 48 may then be increased in size by a small amount using a mechanical, electrochemical or acid etching process, and the blade 34 is then tested again. Other surface features, such as the external aerodynamic surfaces 36, 38, 40, 42 may also require adjustment by removal of small amounts of material following testing.

However, prior methods of removing small amounts of material from the blade 34 to enlarge the holes 48 or change the dimensions of other surface features produce unwanted disruption of the surface properties of the blade, which therefore decreases the accuracy of the tests. It is also difficult using conventional mechanical methods to remove sufficiently precise small amounts of material. Electrochemical processes are generally energy intensive and slow. Acid etching requires the use of hazardous chemicals, and thereby introduces hazards to the user, and increased costs due to the requirements for safety equipment and safe disposal of chemicals.

The present invention describes a method of machining a surface feature of a nickel alloy component of a gas turbine engine, which seeks to overcome some or all of the above problems.

SUMMARY OF THE INVENTION

According to a first aspect of the present invention, there is provided a method of machining a surface feature of a nickel alloy component of a gas turbine engine comprising: providing a gas turbine engine component comprising a nickel alloy; applying a material removal gas comprising gaseous carbon monoxide at a nickel carbonyl gas forming temperature to a surface of the component to form a nickel carbonyl gas and thereby remove a surface layer from at least part of the component.

Advantageously, the process provides a method of removing small amounts of material from a nickel alloy component. The amount of material removed can be very small and controllable, permitting high accuracy. The process may not involve the release of any highly toxic materials, and can be done relatively quickly and inexpensively.

The nickel carbonyl forming temperature may be between 50° and 150° Celsius, dependent on pressure. Higher pressure increases the drive for liquification, higher temperature increases the drive for vapourisation. Preferably, where the process is carried out at standard atmospheric pressures, the nickel carbonyl forming temperature may be between 50° and 60° C.

The method may further comprise at least one testing cycle, each testing cycle comprising applying a testing fluid across a surface of the component and measuring the flow of the fluid. The testing cycle may be performed prior to, subsequent to, or simultaneously with the step of applying the material removal gas to remove a surface layer of the component.

Advantageously, the material removal method can be integrated with the testing cycle, with the testing cycle being performed before or after the material removal method to determine the effect of the removal of small amounts of material, or simultaneously, thereby reducing the time taken to test the component.

The surface from which the surface layer is removed may comprise an external surface such as an external aerodynamic surface of the component. Alternatively, the surface from which the surface layer is removed may comprise an internal surface of the component, such as an internal cooling passage.

The component may comprise one or more cooling holes. The surface from which a surface layer is removed may comprise an internal surface of the one or more cooling holes.

The method may further comprise a precipitation step comprising subsequently heating the nickel carbonyl gas to a precipitation temperature such that the nickel carbonyl gas precipitates to form nickel metal and carbon monoxide gas. The precipitation temperature may be between 70° and 250°, and preferably between 220° and 250° C. Advantageously, the high value nickel metal can be recovered subsequent to removal from the nickel alloy component.

The method may comprise a plurality of testing cycles.

The method may further comprise agitating or brushing the surface of the component after the step of forming the nickel carbonyl gas. The step of agitating or brushing the surface may be carried out prior to applying the testing fluid through the one or more holes. Advantageously, any alloying materials present in the nickel alloy will be removed prior to testing the fluid flow through the holes, thereby ensuring a smooth surface finish for testing.

The method may comprise recirculating the carbon monoxide gas formed by the precipitation step to provide carbon monoxide gas for the nickel carbonyl gas forming step.

The material removal gas may be applied to the component by flowing the gaseous carbon monoxide through one or more cooling holes. Advantageously therefore, nickel material is primarily taken from the sides of the holes, rather than from the remainder of the components, thereby ensuring that only the holes of the component are substantially affected by the removal process.

The testing fluid may comprise carbon monoxide. Consequently, the invention provides a method of simultaneously "tuning" cooling holes (i.e. removing material from the sides of the cooling holes to enlarge them), and testing. The invention therefore provides a relatively quick and efficient means of testing a component, since the same apparatus and process steps can be used for the entire process.

The method may comprise controlling a rate of material removal during the material removal step by one or more of controlling the temperature of the material removal gas, controlling the rate of flow of the material removal gas, and controlling the concentration of carbon monoxide in the material removal gas. Consequently, even where the testing fluid comprises carbon monoxide, the rate of material removal can be controlled independently of the flow rate of the testing fluid.

The component may comprise a plurality of cooling holes, and the method may comprise masking one or more cooling holes. Conventionally in flow testing and I or surface machining, one or more cooling holes may be masked in order to test flow through a subset of holes or to prevent surface machining of the masked holes. The material removal process takes place at a relatively low material removal temperature (e.g. 50 to 60° C.), and so conventional masking methods such as glues and tapes can be employed, without damage.

The component may comprise any of a turbine blade, a nozzle guide vane, a combustor and a combustor lining.

DETAILED DESCRIPTION

Figure 1:
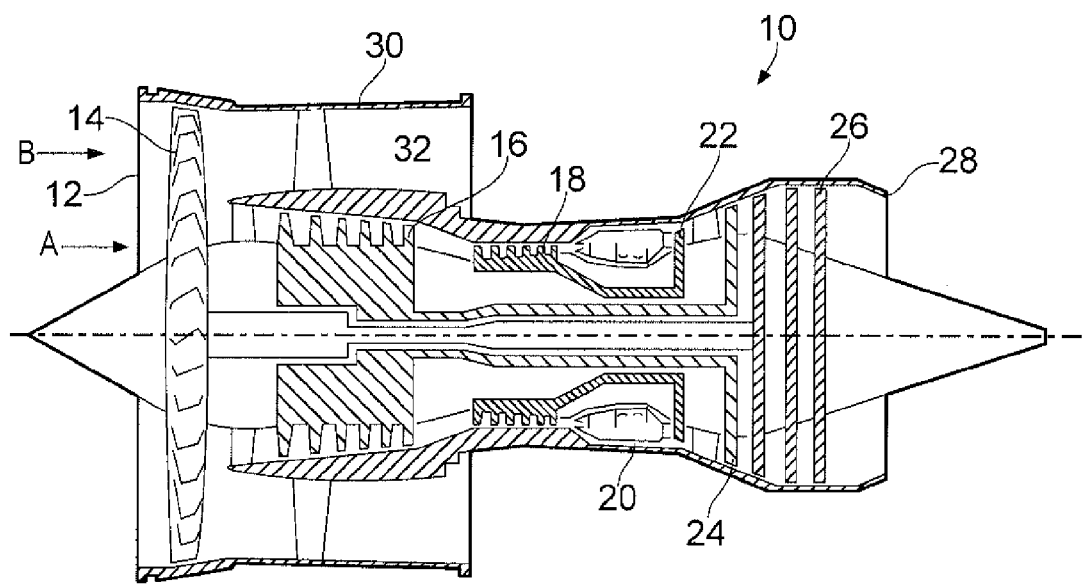
FIG. 1 shows a schematic cross sectional view of a gas turbine engine.

Referring to the drawings, there is described a component of a gas turbine engine, and a method of testing the component.

FIG. 1 shows a gas turbine engine 10. The engine 10 comprises an air intake 12 and a propulsive fan 14 that generates two airflows A and B. The gas turbine engine 10 comprises, in axial flow A, an intermediate pressure compressor 16, a high pressure compressor 18, a combustor 20, a high pressure turbine 22, an intermediate pressure turbine 24, a low pressure turbine 26 and an exhaust nozzle 28. A nacelle 30 surrounds the gas turbine engine 10 and defines, in axial flow B, a bypass duct 32.

Figure 2:
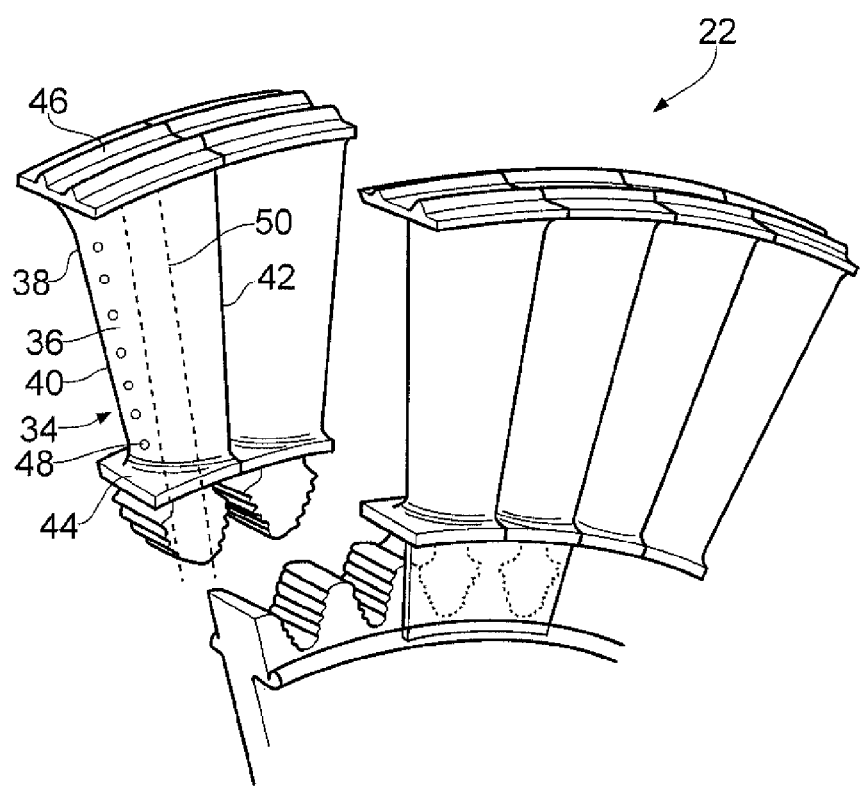
FIG. 2 shows a perspective view of a turbine blade of the gas turbine engine of FIG. 1.

FIG. 2 shows a turbine blade 34 of the high pressure turbine 22. The blade 34 comprises a suction side 36 and a pressure side 38, as well as leading and trailing edges 40, 42, a root 44 at a radially inner end, and a tip 46 at a radially outer end.

The turbine blade 34 includes a plurality of cooling holes 48 leading from an internal passage 50, which extends from the root 44 to the tip 46. The holes 48 provide cooling air provided from one of the compressors 16, 18 to prevent softening of the metal in use, since gases flowing over the turbine blades 34 are generally at a very high temperature. The turbine blade 34 (or at least the internal surfaces of the holes 48 of the blade 34) comprises a nickel containing alloy, such as a nickel superalloy.

Figure 4:
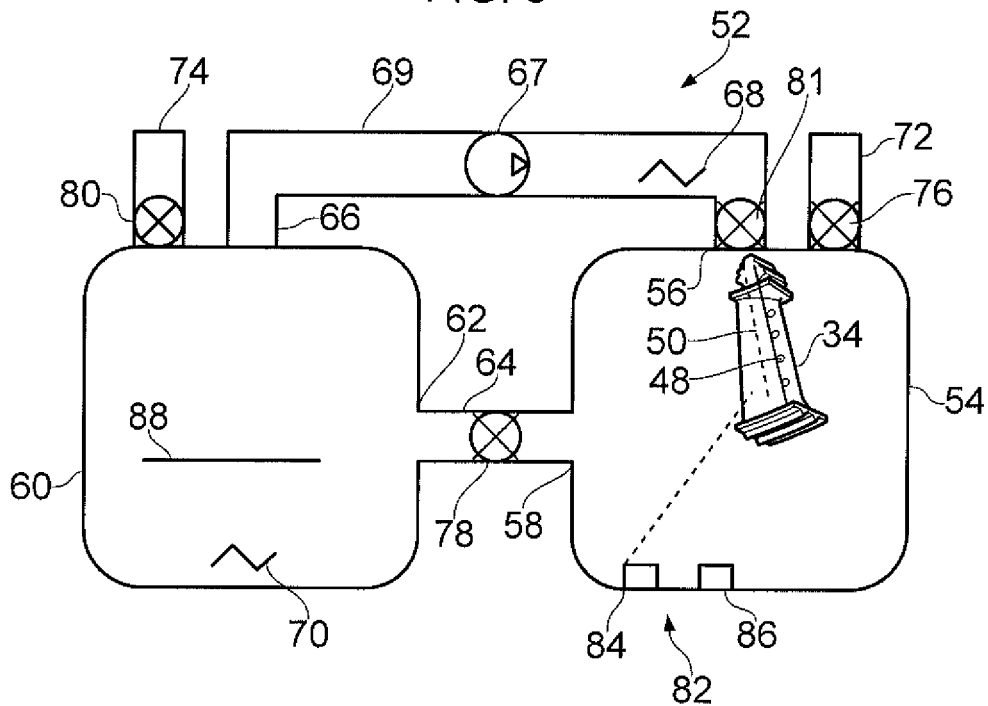
FIG. 4 is a cross sectional view of an apparatus for carrying out the method of FIG. 3.

FIG. 4 shows an apparatus 52 for surface machining and flow testing of the cooling holes 48 of the blade 34. The apparatus 52 comprises a first container 54 in which a turbine blade 34 is located. The container also comprises an inlet 56 into which a material removal fluid can be passed. The blade 34 is placed over the inlet 56, such that the material removal fluid flows in use from the inlet 56 into the internal passage 50 of the blade 34, and then out the one or more of the cooling holes 48. An outlet 58 is also provided, which allows the material removal fluid to escape from the container 54. Alternatively, the material removal fluid could be caused to flow in the opposite direction.

The apparatus 52 further comprises a second container 60 comprising an inlet 62. The inlet 62 communicates with the outlet 58 of the first container 54 via a first tube 64. An outlet of the 66 of the second container 60 is provided, which communicates with the inlet 56 of the first container 54 via a second tube 69. A pump 67 is provided in the second tube 66 to pump fluid around a loop comprising the first and second containers 54, 60 and tubes 64, 69. First and second heaters 68, 70 are provided in thermal contact with respective containers 54, 60 for controlling the temperature of the fluid entering the respective containers 54, 60.

The apparatus 52 includes a gas canister 72 connected to the inlet 56 of the first container 54, and an exhaust 74 connected to the second container 60 for venting gasses to atmosphere or to a scrubber to remove toxic gasses, or recycle them for further use in the apparatus 52. Valves 76, 78, 80, 81 may be provided for controlling gas flow and pressure through the system.

A flow meter is 82 is provided for measuring the flow through the cooling holes 48. The flow meter could comprise a structured light source 84 and detector 86 for determining fluid flow through individual cooling holes 48. Alternatively or in addition, a flow meter could be provided in one of the tubes 64, 69 to determine the overall flow rate through the cooling holes 48.

Figure 3:
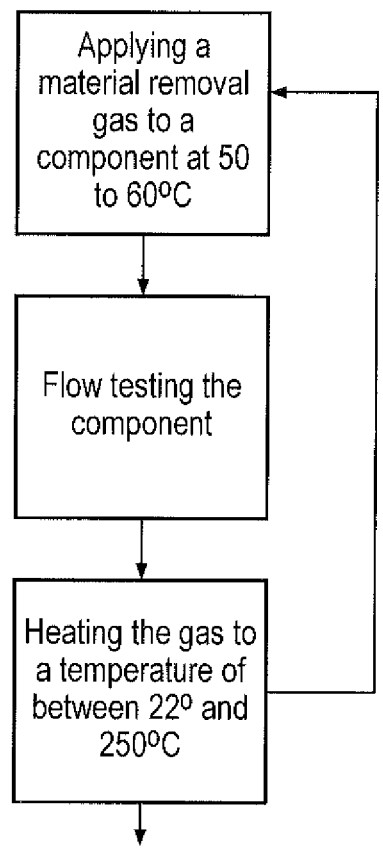
FIG. 3 is a flow diagram illustrating a method in accordance with the present invention.

FIG. 3 describes an exemplary flow testing cycle for surface machining and testing flow of a flow testing gas through the holes 48 of the blade 34, and surface machining of the component using a material removal gas utilising the apparatus 52. In this embodiment, the flow testing gas comprises the material removal gas, through separate gasses could be utilised for material removal and flow testing. The cycle may be continuous, with each step occurring simultaneously, or the steps may be carried out one after the other in a batch process. In the described embodiment, flow testing is carried out prior to material removal—however, it will be understood that material removal could be carried out prior to flow testing, during flow testing or after flow testing.

Prior to carrying out the testing cycle, a blade 34 is designed and manufactured and placed in the first container 54. One or more cooling holes 48 may be temporarily sealed by, for example, tape. Consequently, individual holes 48 or groups of holes 48 can be tested. Parts of the aerodynamic surfaces 36, 38, 40, 42 may also be covered by tape to control the surfaces from which material is removed.

A material removal gas is introduced through the inlet 56 of the first container 54 at a relatively low temperature, such as below the lower bound of the material removal temperature (50° C.). The material removal gas may be transferred into the container 54 from the gas canister 72, or may be pumped from the second container 60 by the pump 67. The material removal gas comprises carbon monoxide, and may comprise a mixture of carbon monoxide and other gasses such as carbon dioxide and nickel carbonyl.

The material removal gas is flowed into the inlet 56 of the first container 54, through the passage 50, and out the non-covered holes 48. The flow continues out through the outlet 58 and through the flow meter 82, where the flow is measured and recorded. The flow continues into the second container 60, and then back through the second tube 66, pump 67, and inlet 56. The flow is continued until satisfactory flow testing data is acquired.

Once satisfactory flow testing data is acquired, material is removed from the holes 48 to widen the holes 48, and thereby acquire another set of data for the larger holes 48. The material is removed from the holes 48 by holding the material removal gas at an above atmospheric pressure and heating the material removal gas flowing into the inlet 56 to a material removal temperature (e.g. 50° to 60° C.) by the first heater 68 such that nickel carbonyl gas is formed by reaction of the carbon monoxide in the material removal gas with the nickel in the nickel superalloy of the blade 34, in accordance with the following reaction:

$$Ni(s) + 4CO(g) \rightarrow Ni(CO)_4(g) \quad (1)$$

The nickel carbonyl enriched material removal gas then flows into the second container 60. The gas in the second container 60 is heated to a decomposition/precipitation temperature (e.g. between 200° and 250° C.) by the second heater 70, and again held at an above atmospheric pressure such that at least some of the nickel carbonyl gas decomposes to nickel and carbon monoxide in accordance with the following reaction:

$$Ni(CO)_4(g) \rightarrow Ni(s) + 4CO(g) \quad (2)$$

The process may be configured to produce relatively pure nickel powder within the second container 60, or to deposit nickel onto a substrate 88 located within the second container 60. In one example, a further turbine blade 34 may be located within the second container 60, such that air flowing into the second container 60 through the inlet 62 flows through the cooling holes 48 of the blade 34, such that nickel metal is deposited on the cooling holes 48, thereby reducing the diameter of the holes 48.

The carbon monoxide is then cycled back round, through the pump 67, and back into the inlet 56 of the first container 54, where further material is removed from the internal surface of the cooling holes 48. The flow meter 80 may be employed during the material removal process to acquire flow data during the material removal process, thereby saving time, and permitting the apparatus 52 to remain sealed during the process. Consequently, the material removal gas and flow testing gas are the same.

During the material removal process, the material removal rate can be controlled by controlling one or more of the temperature and the flow rate of the material removal gas entering the passage 50, such that more or less nickel carbonyl is formed in accordance with reaction (1). In particular, by adjusting the temperature of the material removal gas, the material removal rate can be adjusted independently of the gas flow rate. The material removal rate may be monitored by any one of imaging the holes, decomposing the carbonyl onto a precision balance fringe interferometry, quartz crystal thickness measurement and stiffness change measurement. An impedance measurement may be industrially practical in-process measure (for high purity nickel). For this monitoring method, a crystalline substrate or replenishable wire could be used. A preferred method is to monitor the flow through the holes in the component itself such that the metal removal process signals the component conformance improvement. i.e. monitor the behaviour of the holes in a gas flow regime.

Decomposition is supported by short wavelength light (UV), this could be incorporated as an option for safety, feature localisation, reduced system pressure or system cost.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the scope of the invention.

For example, different components of the gas turbine engine could be flow tested in accordance with the present invention. Particular examples include combustors and combustor linings. The process could be carried out in a single chamber in a batch process, with the temperature being controlled to determine whether nickel carbonyl gas is formed (and so material removed) or nickel powder deposited. The testing gas could comprise a different gas from the material removal gas, such as steam or high pressure air.

The invention claimed is:

1. A method of flow testing cooling holes of a nickel alloy component of a gas turbine engine comprising: providing a gas turbine engine component comprising a nickel alloy; applying a material removal gas comprising gaseous carbon monoxide at a temperature of between 50° and 60° Celsius to a surface of the component to form a nickel carbonyl gas and thereby remove a surface layer from at least part of the component, wherein the component comprises one or more cooling holes, and the surface from which a surface layer is removed comprises an internal surface of the one or more cooling holes, and wherein the method further comprises at least one testing cycle, each testing cycle comprising applying a testing fluid through the cooling holes of the component and measuring the flow of the fluid.

2. A method according to claim 1, wherein the nickel carbonyl forming temperature is between 50° and 60° Celsius.

3. A method according to claim 1, wherein the surface from which the surface layer is removed comprises an external surface of the component.

4. A method according to claim 1, which further comprises a precipitation step comprising heating the material removal gas to a precipitation temperature between 220° and 250° C.

5. A method according to claim 1, which further comprises agitating or brushing the surface of the component after the step of forming the nickel carbonyl gas.

6. A method according to claim 4, which further comprises recirculating the carbon monoxide gas formed by the precipitation step to provide carbon monoxide gas for the nickel carbonyl gas forming step.

7. A method according to claim 1, wherein the testing fluid comprises carbon monoxide.

8. A method according to claim 1, wherein the method comprises controlling a rate of material removal during the material removal step by one or more of controlling the temperature of the material removal gas, controlling the rate of flow of the material removal gas, and controlling the concentration of carbon monoxide in the material removal gas.

9. A method according to claim 1, wherein the component comprises a plurality of cooling holes, and the method comprises masking one or more cooling holes.

10. A method according to claim 3, wherein the external surface is an external aerodynamic surface of the component.

11. A method according to claim 1, wherein the component comprises any of a turbine blade, a nozzle guide van, a combustor and a combustor lining.

An examiner's amendment to the record appears below. Should the changes and/or additions be unacceptable to applicant, an amendment may be filed as provided by 37 CFR 1.312. To ensure consideration of such an amendment, it MUST be submitted no later than the payment of the issue fee.

* * * * *